United States Patent [19]

Dorn et al.

[11] Patent Number: 4,980,057
[45] Date of Patent: Dec. 25, 1990

[54] APPARATUS FOR MASS SPECTROMETRIC ANALYSIS OF LIQUID CHROMATOGRAPHIC FRACTIONS

[75] Inventors: Steven B. Dorn; Woodfin V. Ligon, Jr., both of Schenectady, N.Y.

[73] Assignee: General Electric Company, Schenectady, N.Y.

[21] Appl. No.: 416,682

[22] Filed: Oct. 3, 1989

[51] Int. Cl.5 .................. B01D 15/08; B01D 59/44
[52] U.S. Cl. .................. 210/198.2; 55/257.1; 55/261; 55/267; 55/277; 210/149; 210/177; 210/180; 250/288
[58] Field of Search .............. 55/15, 17, 257.1, 261, 55/277, 267; 210/656, 748, 198.2, 149, 177, 180, 182; 250/281, 282, 288, 288 A

[56] References Cited

U.S. PATENT DOCUMENTS

| | | | |
|---|---|---|---|
| 4,014,793 | 3/1977 | Tesarik et al. | 210/198.2 |
| 4,112,297 | 9/1978 | Miyagi et al. | 250/288 A |
| 4,280,823 | 7/1981 | Szonntagh | 210/748 |
| 4,570,068 | 2/1986 | Sakairi et al. | 250/288 A |
| 4,582,654 | 4/1986 | Karnicky et al. | 261/DIG. 48 |
| 4,607,163 | 8/1986 | Mizuno | 250/288 A |
| 4,629,478 | 12/1986 | Browner et al. | 55/257.1 |
| 4,654,052 | 3/1987 | Sharp | 210/656 |
| 4,863,491 | 9/1989 | Brandt et al. | 55/15 |

Primary Examiner—Peter Hruskoci
Attorney, Agent, or Firm—Sudhir Deshmukh; James C. Davis, Jr.; William H. Pittman

[57] ABSTRACT

An apparatus for combining a liquid chromatograph and a mass spectrometer is described. The liquid chromatograph elution solvent is removed and sample particles are carried to the mass spectrometer relatively free of solvent.

13 Claims, 3 Drawing Sheets

APPARATUS FOR MASS SPECTROMETRIC ANALYSIS OF LIQUID CHROMATOGRAPHIC FRACTIONS

BACKGROUND OF THE INVENTION

This invention relates to an apparatus for interfacing a liquid chromatograph with a mass spectrometer. More particularly, the present invention is directed to the combined facilities of a liquid chromatograph and a high resolution double-focusing mass spectrometer. The method of the invention includes volatilizing a liquid chromatograph eluate, separation of the solvent liquid, and transport of high boiling substances of interest to the mass spectrometer in the form of suspended particles for analysis.

Mass spectrometric analysis of gas chromatograph fractions is known. It has been recognized that certain classes of organic substances while amenable to mass spectrometric analysis cannot be separated by passing through a gas chromatograph. Therefore, some other means of separating such materials is required as preparation for mass spectrum studies and identification.

A common method for separating such materials is by liquid chromatography. Liquid chromatography is a technique which is useful in analyzing substances which comprise large or polar molecules and therefore unsuitable for gas chromatography.

Liquid chromatography provides a means for separating complex mixtures of either organic or inorganic mixtures into their various components, for example, compounds that are thermally unstable or nonvolatile under normal gas chromatographic conditions.

Another widely used technique for providing structural information about chemical species is mass spectrometry. Mass spectrometry identifies unknown species by comparison of its mass spectrum with a reference mass spectrum obtained from a known composition. Mass spectrometry generally requires that the mass spectra be generated by the electron impact mode of ionization and mass spectra should be limited to only one species at a time In liquid chromatography, a chromatographic solvent containing a mixture of components in solution, is passed through a chromatographic column. The chromatographic column is designed so that it separates the mixture, by differential retention on the column, into its various components. The component species emerge from the column as distinct bands in the solvent stream separated in time and therefore distinguishable by the relative retention times. Thus, a liquid chromatograph provides a means for introducing single species of substances which have been separated from an initially complex mixture into a mass spectrometer.

While liquid chromatography provides a means for separating a mixture into its components, in order for an accurate mass spectrum of the various components to be obtained, the chromatographic solvent remaining in the eluent must be separated and removed from the material delivered to the mass spectrometer. Without removal of the solvent from the material entering the ionization chamber of the mass spectrometer, the mass spectra obtained cannot be used for precise identification of the compounds or materials.

The organic liquids that are used as eluents in liquid chromatography, if present even in minute amounts, constitute a major source of error in any subsequent mass spectrometric analysis. This occurs because the material entering the mass spectrometer exits the liquid chromatograph in the form of a solution which generally has a concentration in the range of 10–100 parts per million (ppm) of eluent. As a result, an interfacing means and method which removes the solvent while efficiently transferring the material of interest to the mass spectrometer is needed and is provided by this invention.

One approach to the removal of solvent from a sample prior to mass spectrometry is disclosed in U.S. Pat. No. 4,629,478 which shows a constant flow of solvent solution containing the material to be analyzed to a monodisperse generator. The monodisperse generator generates droplets of particles of both solvent and solute which have a narrow range of sizes. The finely dispersed solvent aerosol is diluted with a gas, usually an inert gas such as argon or helium, and passes into a low pressure desolvation chamber. In the desolvation chamber, the majority of the solvent evaporates and is separated from the solute, i.e., the material to be analyzed by the mass spectrometer. The combination of dispersion gas and solvent vapor then passes sequentially through two pressure reduction chambers where the dispersion gas and solvent vapor is removed by vacuum pumps. A highly dispersed aerosol of sample material remains after solvent evaporation in the vacuum chambers. This aerosol enters the ionization chamber of the mass spectrometer where ions are generated for subsequent mass analysis.

Another design for an interface utilizing particle beam technology is currently marketed by Hewlett-Packard Company. This device uses a pneumatic nebulizer and a two-stage momentum separator. The stated sensitivity specification for the Hewlett-Packard device is a signal/noise ration of 50:1 on the molecular ion of caffeine using a sample size of $20 \times 10^{-9}$ g. and an LC flow of 0.5 ml/min. methanol.

Other techniques for combining liquid chromatographs and mass spectrometers are disclosed in Winkler et al., 60 Anal. Chem. 489–93 (1988) and Willoughby et al., 56 Anal. Chem. 2626-2631 (1984). In Winkler the effluent from the liquid chromatograph column is pumped through a small diameter orifice thereby forming a liquid jet. The liquid jet spontaneously breaks through Rayleigh interactions with the surrounding gas. The stream is subjected to a perpendicular flow of helium gas which disperses the particles. The primary drop stream is then subjected to a secondary shearing force which reduces drop size. Upon travelling to an unheated desolvation chamber the stream passes to a two stage momentum separator.

Willoughby discloses a two-stage aerosol-beam separator in conjunction with a monodisperse aerosol generator and a desolvation chamber. Heat is applied to the desolvation chamber by means of a heating tape wrapped around the chamber.

SUMMARY OF THE INVENTION

This invention which contemplates providing a substantially solvent-free sample of a high boiling organic or inorganic chemical species or compound in finely divided particulate for delivery to the ion chamber of a mass spectrometer comprises liquid chromatograph means for separating dissolved chemical species, nebulizer means for forming an aerosol comprising the chemical species in solution, desolvation means for vaporizing the solvent into liquid droplets distinct from solid particles of the chemical species, separation means for separating liquid droplets from solid particles and delivering a beam of solid particles to a mass spectrometer. The invention includes an apparatus which provides the interfacing of a liquid chromatograph with a high resolution double focusing mass spectrometer. The apparatus provides volatilization of the liquid chromatography elution solvent while retaining high boiling sample material, e.g., a chemical species or compound to be identified in the form of small suspended particles. The small particles are formed from an aerosol generated by an improved ultrasonic nebulizer. After formation, these particles and the solvent vapor are drawn through a small orifice under the influence of a vacuum. The orifice causes the sample particles to form a beam which travels through three pumping stages of a momentum separator thereby reaching the mass spectrometer substantially free of solvent. The heat necessary for vaporization of the solvent can be provided by a feedback controlled heater within the desolvation chamber.

OBJECTS OF THE INVENTION

It is an object of the invention to provide an apparatus for removing the liquid chromatograph solvent without the loss of sample material.

It is an object of the invention to provide an apparatus for efficiently transferring a sample material to a mass spectrometer for analysis.

It is a further object of the invention to provide an apparatus which is relatively insensitive to the type of solvent used in the liquid chromatography and which produces unusually low final pressures of solvent at the mass spectrometer.

It is also an object of the present invention to provide an improved ultrasonic nebulizer.

DETAILED DESCRIPTION OF THE INVENTION

Figure 1:
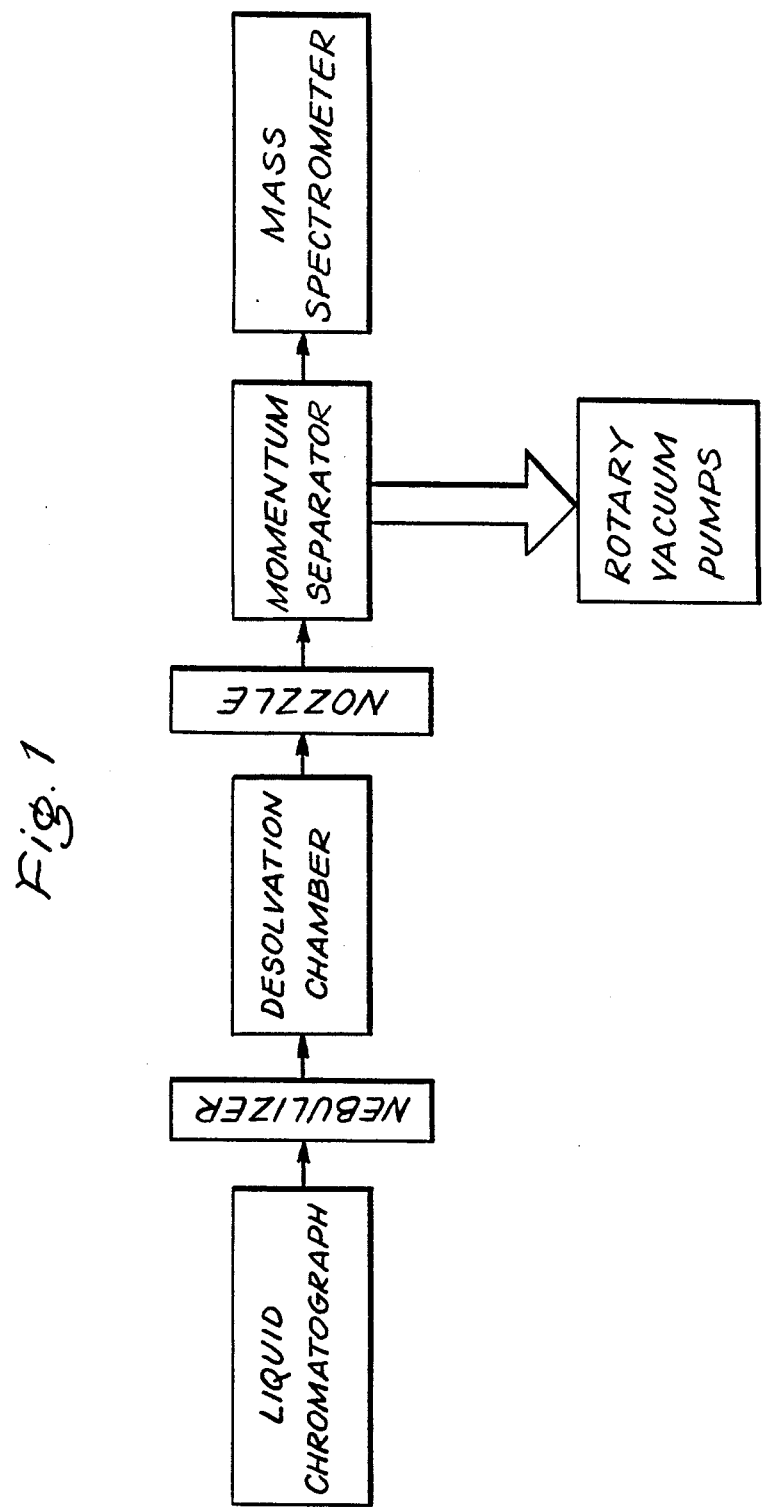
FIG. 1 is a block diagram of the apparatus of the present invention.

FIG. 1 shows a block diagram showing generally the path of travel of the material to be tested in the apparatus of the present invention. The material to be tested is initially isolated in the liquid chromatograph. The sample solute-containing liquid chromatograph elution solvent then passes to a nebulizer means for volatilizing the liquid chromatograph eluate solution such as an ultrasonic nebulizer. The volatilizing means forms an aerosol comprising the liquid chromatograph solution of the high boiling material in the form of small suspended droplets. After formation in the volatilizing means, the aerosol passes through desolvation means such as a desolvation chamber in which the solvent is vaporized through evaporation leaving the material to be analyzed by the mass spectrometer in the form of solid particles carried by the stream of vapor and nebulizer gas. Evaporation of the solvent may cause cooling of the solvent sufficient to result in reduced evaporation. Heat, as needed, is provided by heating the mixture of vapor and inert carrier gas, usually helium. As the particles reach the end of the desolvation chamber, the solid particles are almost completely solvent-free when at the entrance to the nozzle of the momentum separator. The pumping action of the momentum separator causes the solid particles to accelerate to sonic velocities. As the particles accelerate, the solvent vapor and carrier gas are extracted from the stream by vacuum pumps as described more fully below. The solvent-free sample then travels as a beam of particles into the mass spectrometer for analysis.

The liquid chromatograph may be of any conventional design such as a Waters model 600 MSTN and the chromatograph may also include a UV detector such as Waters model 484 MS UV detector connected in series just before the nebulizer of the interface apparatus. In the preferred embodiment, it is essential that the UV detector be capable of operating under sustained back pressures of several thousand psi without damage.

Figure 2:
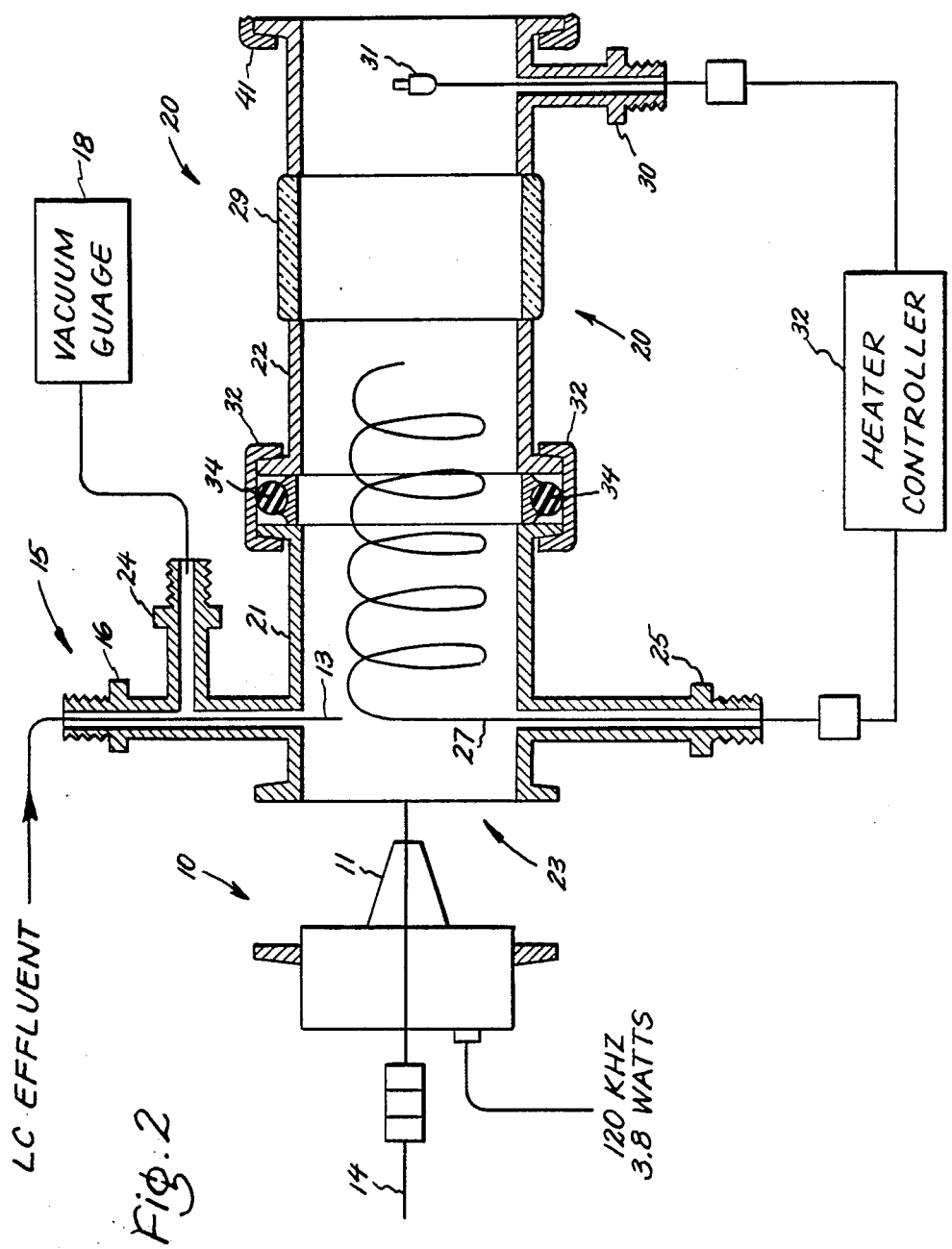
FIG. 2 is a detailed drawing of the nebulizer and desolvation chamber.

FIG. 2 shows a volatilizing means or nebulizer 10 and desolvation means or chamber 20. The volatilizing means 10 is mounted for stability, such as on a conventional KF-40 flange (not shown), and can be a standard commercial unit obtained from Sonotek Corporation, such as their model 8700. The nebulizer is modified to provide the improved results of the present invention.

In the volatilizing means of the present invention, the liquid is delivered obliquely or orthogonally to the tip of the ultrasonic horn 11 rather than axially as is the case in commercial nebulizers. This is accomplished by means of a supply tube which is directed substantially perpendicular or at an acute angle with respect to the flow of inert gas. The manufacturer of the nebulizer intends for the liquid to be supplied axially to the tip 11, via a compression fitting at the rear of the unit. It has been found that because the nebulizer must operate in a partial vacuum, this method of liquid introduction is not satisfactory. Extensive "bumping" of solvent may be experienced which may result in serious disruption of the nebulizer operation. In order to avoid this problem, a very narrow capillary tube 13 is employed to deliver the eluent. The capillary maintains a high pressure and prevents bumping.

Prior art nebulization methods are either pneumatic or thermal (i.e. thermospray). In the present invention, the volatilizing means is a hybrid which is both ultrasonic and pneumatic. Accordingly, the volatilizing means is far less solvent dependent than the prior art nebulizers. It has been found that the liquid chromatograph effluent should be rerouted through a tube 13 which is mounted on chamber 20. The tube assembly 15 comprises compression fitting 16 and 17.

This tube assembly consists of a stainless steel outer portion having 1/16" o.d. and 0.009" i.d. and an inner portion consisting of a 0.1 mm i.d. fused silica capillary tube 13. The stainless steel portion serves to support and align the fused silica tube. The stainless steel outer portion extends to within about 2 mm of the nebulizer tip 11 while the fused silica tube 13 extends beyond the stainless steel outer portion to within 0.5 mm of the nebulizer tip 11 when the nebulizer unit is inserted in place in desolvation chamber 21. The fused silica tube is connected to the output of the liquid chromatograph detector (LC effluent). This very small inlet line produces large back pressures at the outlet of the liquid chromatograph detector. By keeping the solvent under high pressure until it reaches the nebulizer tip 11, this procedure eliminates the bumping phenomenon that had previously been experienced.

The invention may also include a means for adding a second solvent stream directly at the nebulizer by means of a similar tube assembly and compression fitting.

All other types of nebulizer generally need to combine solvent streams before reaching the nebulizer. The early combination of stream allows for the possibility of solvent/solute incompatibility resulting in precipitation of solute with the possible effect of encountering clogged lines. Mixing on the nebulizer surface eliminates this problem. The mixing of a second flow of solvent also may be used to reduce peak broadening by providing a rinsing function of the nebulizer surface without loss of sensitivity.

The second tube assembly, not shown, is composed of an identical stainless steel outer tube and fused silica inner tube also positioned to deliver liquid to the tip of the volatilizing means. The second Swagelok-type fitting can be provided on the KF-40 flange for attachment of tube assembly. This second tube assembly provides a means for connecting the effluent of a second liquid chromatographic pump. This second pump may be used to provide a second flow of solvent or solvent plus an additive.

Addition of the second solvent stream at the volatilizing means itself instead of at some earlier point ensures that the added solvent or solvent plus additive cannot have detrimental effects on the UV detector response and cannot cause precipitation of solute in the detector or in the interconnecting lines.

In order to disperse the aerosol, the original liquid supply connection of the nebulizer is used to supply a jet of an inert gas, such as helium, from tank to the nebulizer tip 11. This is accomplished by providing a 0.32 mm inner diameter fused silica tube 14 inside the nebulizer's original axial supply orifice to a point approximately 1 cm back from the nebulizer tip. The fused silica line is held in a well centered position within the original axial supply tubing by a compression union. The inside diameter of the central portion of the union is reduced so that it approaches the outside diameter of the fused silica tubing thereby providing a means for supporting the fused silica tube which provides enough restriction to give a high gas velocity at the desired flow rates of inert gas. The inert gas flow rates in use currently fall in the range of about 1 liter/min. However, rates ranging from 300 ml to several liters per minute can be used.

The desolvation means 20 consists of two parts or chambers 21, and 22, each of which consists of a 1.4 in. inner diameter tube fitted at each end with flanges. Section 21 of the desolvation means 20 houses the nebulizer at one end 23 and is also fitted with two or three compression type fittings 24 and 25. Fitting 24 serves as the connection to a vacuum gauge 18. Fitting 25 has inserted therein a heater 27, preferably a coiled heater such as a 3 foot long by 1/16 in. calrod type stainless steel heater obtained from Watlow Inc.

Prior systems heated the walls of the chamber and did not include an internal heating means positioned within the desolvation means. A coiled heater within the desolvation means is considerably more effective and permits more accurate temperature control through the use of a feedback temperature controller. The heater 27 enters through fitting 25 and is then positioned in the free space inside the desolvation chambers 21 and 22.

The second chamber 22 of the desolvation means 20 can be fitted with a sealed glass section 29 near its center which allows for a visual evaluation of the relative dryness of the aerosol being produced in the chamber. In addition, this part of the desolvation means is preferably fitted with a suitable compression fitting 30 for mounting of a thermocouple probe 31, preferably just in front of the entrance to the nozzle of the momentum separator shown in FIG. 3. The thermocouple is used to sense the temperature of the gas just before the nozzle of the momentum separator. The temperature of the gas at that point is used to control the current applied to the heater. The output of this thermocouple 31 is monitored by a temperature controller 32 to modulate the current supplied to the heater mounted in the desolvation chamber. The temperature of the inert gas/solvent vapor mix is usually set to a temperature between 80° and 90° F. using this temperature controller 32.

Chambers 21 and 22 are joined by flange means 32 and centering rings not shown which include O-rings 34. Nebulizer means 10 can be mounted onto the desolvation means by the same flange and centering ring means.

Figure 3:
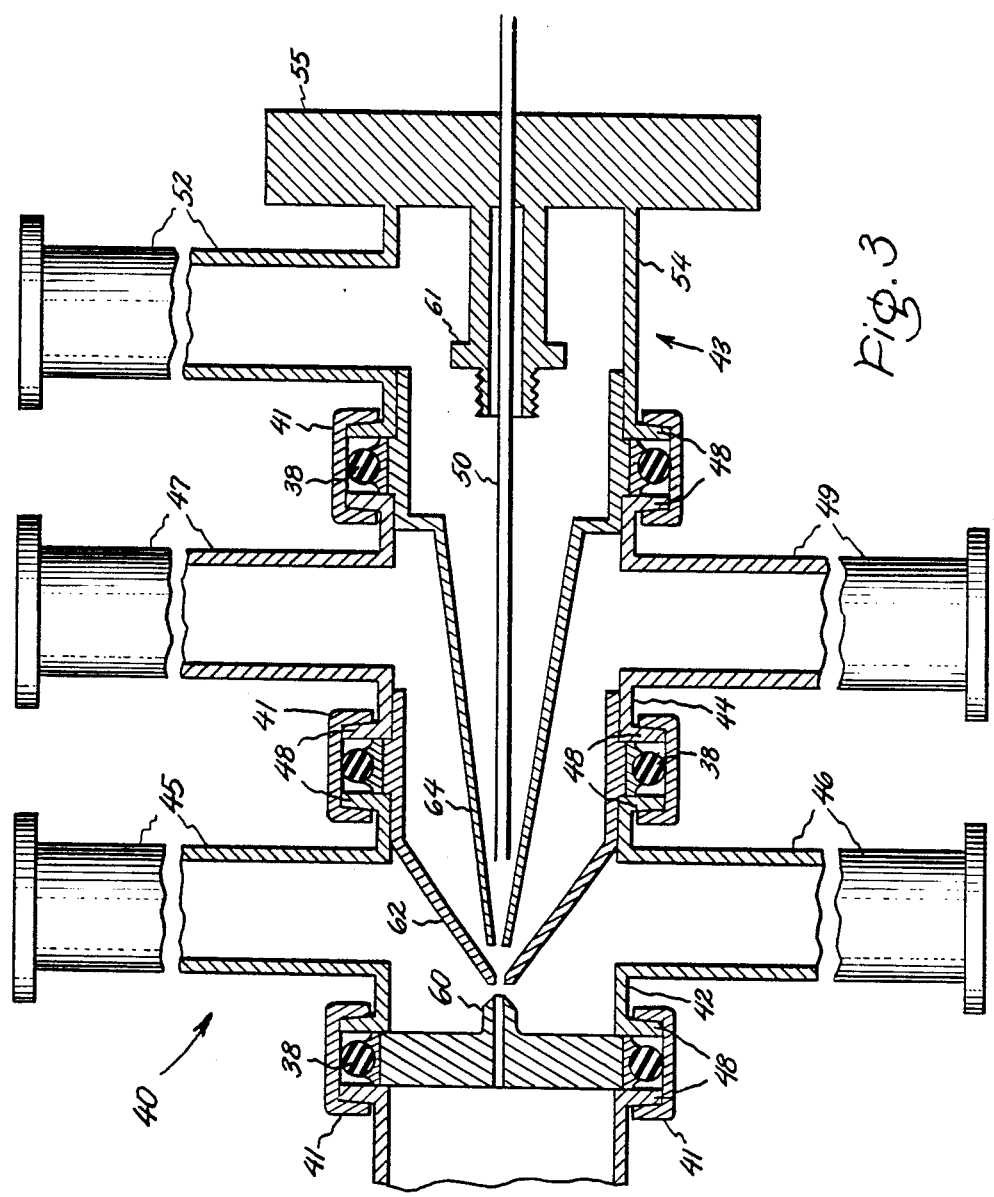
FIG. 3 is a detailed drawing of the momentum separator.

Turning to FIG. 3, desolvation chamber 22 mounts directly to the momentum separator 40 by means of end flange 41 and O-ring 38. The momentum separator 40 preferably comprises seven features. The first three constitute the housing of the device. Two of these parts (42, 44) are almost identical and consist of stainless steel tubing fitted at each end with flange 48. These parts are also fitted with two oppositely disposed tubes 45, 46, 47, and 49 which serve as connecting lines to the vacuum pumps (not shown) which evacuate the various stages of the momentum separator. On each section, the two pumping lines are connected to a common 20 cubic foot per minute rotary vacuum pump and can be isolated from the pump using a conventional vacuum valve which is installed in each vacuum supply line. One of these housings can also be fitted with a compression fitting, not shown, which allows the installation of an internal heater which could be used to heat the first stage if icing becomes a problem.

A third stage, vacuum line 52, of pumping in the momentum separator is used to reduce pressures to the range necessary for operation of high performance magnetic mass spectrometers. The pumping restriction between the third pumping stage and the ion source of the mass spectrometer is provided by a long inlet line. This line is frequently not necessary to confine the particles as they are usually well collimated but it does provide the needed pumping restriction.

The third housing section 43 of the momentum separator consists of a stainless steel tube 54 fitted at one end with a KF-40 flange 48 and at the other end with a 4 in. gold "O" ring sealed vacuum flange 55 arranged to mate to a 30 similar flange on the housing of the mass spectrometer. This section of the housing is also fitted with a 0.6 in. inner diameter pumping line 52. In operation, this pumping line is attached to a 8 cu. ft/min rotary pump. The gold "O" ring flange is fitted with an internal axially-positioned compression type fitting 61 which serves as a mount for the glass inlet 50 line which conveys the particle beam into the mass spectrometer.

Three of the remaining 4 parts of the momentum separator are arranged to mount inside of and be firmly attached to centering rings of the flanges, are the nozzle 60, the first skimmer 62, and the second skimmer 64. The nozzle 60 has an inside diameter of approximately 0.5 mm and a length of 0.5 in. The first skimmer 62 has an inside diameter at the tip of 0.5 mm. In addition, the angle observed at the tip of a conic section which bisected the first skimmer would be preferably about 67 degrees. The second skimmer 64 which has an inside diameter at the tip of about 1.0 mm. The angle observed at the tip of a conic section which bisected the second skimmer would be preferably about 16 degrees. The final component of the momentum separator consists of a glass tube 50. This glass tube mounts in fitting 61 at the gold "O" ring flange end of the final housing part. This glass tube serves to conduct the particle beam from near its exit behind the second skimmer 64 to a point approximately 1 centimeter from the side of the mass spectrometer's ion source block. Because of its small inside diameter, the glass tube also serves as a restriction to isolate the final pumping stage of the momentum separator from the high vacuum of the mass spectrometer's ion source.

When all of the mechanical components are connected using KF type flanges, each of the parts can be readily demounted for adjustment or modification. The positions of each of the skimmers, the nozzle and the glass inlet line are all adjustable horizontally along the axis of the momentum separator. The preferred positions of the various components are as follows: (1) Nozzle 60 centered horizontally in its centering ring arbitrarily defined as reference position "O" in. (2) The first skimmer 62 about 3 mm behind the tip of the nozzle. (3) The second skimmer 64 about 5 mm behind the nearest point of contact between the tip of this skimmer and the inside wall of the first skimmer 62. (4) Inlet line 50 about 5 mm behind the nearest point of contact between the tip of the inlet line and the inside wall of the first skimmer 62.

Minor adjustments in the axial alignments of the nozzle and the various skimmers are possible because of slight side play where the centering rings make contact with the flanges. Using this adjustment, the alignments have been optimized optically to ensure that the orifices are strictly concentric with each other.

The mass spectrometer's ion source was originally provided with two heaters which serve to warm the ion source to temperatures as high as 250° C. It has been found that this heating was not uniform and that the region of the ion source being impacted by the particle beam was not heated sufficiently to provide effective volatilization of the particles. Accordingly, the ion source was modified by providing a gold-plated copper target for the particle beam and relocating one of the two heaters to a location inside this copper target. In addition, the platinum thermometer which monitors the temperature of the ion source and controls the heater current was relocated to a position directly adjacent to the copper target. Using this arrangement, temperatures as high as 300°-350° have been obtained providing effective volatilization of even very high boiling samples.

When operating, the nebulizer is supplied with the output of the liquid chromatograph and with a flow of helium amounting to about 1000 ml/min. With an applied power of about 3.8 watts, the ultrasonic nebulizer produces an aerosol with particle sizes ranging from about 10-50 micron. These particles are dispersed by the helium jet and travel into the desolvation chamber. In the desolvation chamber, these small aerosol particles tend to dry out by losing organic solvent. This causes cooling of the droplet which if not compensated will cause evaporation to cease. The cooling is compensated by providing a heated carrier gas, e.g., helium. The helium itself is heated by the coiled heater described above. Sufficient heat input is ensured by monitoring the temperature of the gas at the end of the desolvation chamber. Significant numbers of aerosol particles are not lost by contact with the heater because as a particle approaches the heater it tends to lose solvent more quickly on the heated side thereby generating an asymmetrical force on the particle with a net vector sum directed away from the hot surface. Under most conditions, the vacuum in the desolvation chamber is about 20 inches of mercury. Care must be taken not to allow the pressure to become too low because this may inhibit drying of the particles by reducing the contact time between the particles and the helium.

In passing through the desolvation chambers, the aerosol becomes completely dried out and appears at the entrance to the nozzle as a mixture of helium, solvent vapor, and small dry particles of sample. The strong pumping of the momentum separator generates a high velocity flow through the nozzle. This accelerates the sample particles to sonic velocities. Because the sample particles are much more massive than the associated inert gas, usually helium gas, and solvent vapor, these particles have much greater momentum and tend to travel in a straight line after leaving the nozzle. On the other hand, the gaseous components of the nozzle jet tend to be pumped away by the action of the rotary vacuum pumps. Most of the gas (97%) is removed in the first stage of the momentum separator. The later stages serve to remove the last traces of solvent vapor and helium leaving the sample particles to continue their trip to the ion source effectively free of solvent vapor. The pressure ultimately obtained in the ion source is about $1 \times 10^{-6}$ torr, which is very near the value observed when the liquid chromatograph is not connected. It should be noted that this value is much better than the pressure obtained by two-stage momentum separators. Typical values for two-stage separators are about $1 \times 10^{-5}$ torr. A good vacuum is necessary for the proper operation of high resolution mass spectrometers which utilize ion sources operating at 8-10 keV.

The advantages of the present invention are due to the use of a specially modified ultrasonic nebulizer instead of a pneumatic nebulizer or a thermospray nebulizer as employed in the prior art, the use of a heater directly in the gas stream of the desolvation chamber and the control of this heater using a thermocouple located near the inlet of the nozzle, the use of a momentum separator in which the skimmers are symmetrically pumped from two directions in order to minimize turbulence and the use of a three-stage momentum separator which produces much lower pressures at the mass spectrometer while maintaining a high yield of sample particles.

The use of an ultrasonic nebulizer gives much greater flexibility compared to other designs because there is no need to readjust the nebulizer temperature when solvents change (gradient elution techniques) as with prior art thermospray nebulizers. Further, using an ultrasonic nebulizer, the inert gas flow may be adjusted at will to accommodate changing LC flow rates and solvent volatility.

We report here measurement of the efficiency of transmission of a solute through the interface.

We have measured the total integrated signal obtained for the substance cholesterol as obtained by evaporation from a solids probe positioned exactly adjacent to the ion source of the mass spectrometer. We have also measured the total integrated signal obtained for cholesterol using the same mass spectrometer when that substance is injected into a liquid chromatograph operating with the solvent methylene chloride at 0.5 ml/min flow rate and fitted to the mass spectrometer via our particle beam type LC-MS interface. We find that the total integrated signal obtained via the LC interface corresponds to 12% of the total integrated signal obtained via the solids probe. Under these conditions the ion source pressure was $1\times10^{-6}$ torr as measured using a penning ionization-type pressure gauge integral with the mass spectrometer.

We claim:

1. An apparatus for interfacing a liquid chromatograph with a mass spectrometer comprising:
   a volatilizing means for volatilizing under partial vacuum a mixture of liquid chromatograph solvent and dispersing the resultant particles by a flow of inert gas to produce an aerosol stream of particles, said volatilizing means including an ultrasonic nebulizer to provide both ultrasonic and pneumatic nebulization of said particles;
   a desolvation means for evaporating liquid chromatograph solvent into gaseous components from said stream, said desolvation means having a heater therein for maintaining through feedback temperature controller means the temperature of said aerosol stream of particles and compensating for the cooling of the stream of effluent due to evaporation of the liquid chromatograph solvent, and
   a momentum separator connected to said desolvation means, said momentum separator having three stages, said momentum separator being capable of accelerating said particles to sonic velocities and symmetrically removing the gaseous components of the liquid chromatograph solvent at each of said stages by means of a vacuum to minimize turbulence.

2. An apparatus according to claim 1 wherein said particles in the aerosol have a particle size in the range of about 10–50 microns.

3. An apparatus according to claim 1 wherein said inert gas is helium.

4. An apparatus according to claim 3 wherein said volatilizing means is capable of producing a flow of said helium at the rate of about 1000 ml/min.

5. An apparatus according to claim 4 wherein said vacuum means in the stages of the momentum separator are rotary vacuum pumps.

6. An apparatus according to claim 1 wherein said momentum separator has skimmers which are symmetrically pumped from two directions.

7. An apparatus according to claim 1 wherein said volatilizing means has a capillary means to deliver chromatograph effluent to the side of an ultrasonic horn of said nebulizer, said nebulizer having means to receive an axial flow of said inert gas to disperse the particles and provide ultrasonic and pneumatic volatilization of said particles.

8. An apparatus according to claim 7 including means for adding a second solvent stream at said ultrasonic horn.

9. An apparatus according to claim 7 wherein said capillary means further comprise a capillary tube.

10. An apparatus according to claim 1 wherein said heater is a coil positioned within said desolvation means.

11. An apparatus according to claim 10 wherein said heater includes means for monitoring said feedback temperature controller means.

12. An apparatus according to claim 11 wherein said controller receives a feedback signal from a thermocouple probe proximal an entrance to said momentum separator.

13. An apparatus according to claim 1 wherein a first stage of said momentum separator includes an internal heater.

* * * * *